US007657075B2

(12) United States Patent
Viswanathan

(10) Patent No.: US 7,657,075 B2
(45) Date of Patent: Feb. 2, 2010

(54) REGISTRATION OF THREE DIMENSIONAL IMAGE DATA WITH X-RAY IMAGING SYSTEM

(75) Inventor: Raju R. Viswanathan, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 865 days.

(21) Appl. No.: 11/429,665

(22) Filed: May 5, 2006

(65) Prior Publication Data

US 2006/0269164 A1 Nov. 30, 2006

Related U.S. Application Data

(60) Provisional application No. 60/678,322, filed on May 6, 2005.

(51) Int. Cl.
*G06K 9/00* (2006.01)
(52) U.S. Cl. ......................... 382/132; 382/131; 600/425
(58) Field of Classification Search ................. 382/131, 382/132; 600/425
See application file for complete search history.

(56) References Cited

U.S. PATENT DOCUMENTS 7,366,278 B2 * 4/2008 Fu et al. ......................... 378/4
7,555,331 B2 * 6/2009 Viswanathan ............... 600/424
2004/0176931 A1 * 9/2004 Wright et al. ............... 702/189
2005/0203384 A1 * 9/2005 Sati et al. .................... 600/426
2006/0025681 A1 * 2/2006 Abovitz et al. .............. 600/425

* cited by examiner

*Primary Examiner*—Vikkram Bali
*Assistant Examiner*—Katrina Fujita
(74) *Attorney, Agent, or Firm*—Harness, Dickey & Pierce, P.L.C.

(57) ABSTRACT

A method for determining a transformation of a three-dimensional pre-operative image data set to obtain a registration of the three-dimensional image data with an X-ray imaging system. In one aspect of the present invention, the method comprises the steps of the user identifying a center point and extreme contour points of the object from an X-ray image, obtaining a set of contour points for the image object in each of a plurality of section-planes, and selecting from a sampling of section-planes the points projecting nearest to the user-identified extreme points. The method then defines a grid having a predetermined number of intervals at a predetermined interval spacing with the grid center at the user-identified center of the pre-operative image, and performs a projection of the center point of the three-dimensional image data set onto each grid point for evaluation and selection of the grid point projecting nearest to the user-identified center. Registration of a three dimensional image data will allow, among other things, overlay of a visual representation of a pre-operative image object onto an X-ray image plane that can serve as a visual tool and a surgical navigation aid.

20 Claims, 3 Drawing Sheets

REGISTRATION OF THREE DIMENSIONAL IMAGE DATA WITH X-RAY IMAGING SYSTEM

CROSS-REFERENCE TO RELATED APPLICATIONS

This application claims the benefit of U.S. Provisional Patent Application Ser. No. 60/678,322, filed May 6, 2005, the entire disclosure of which is incorporated herein.

FIELD OF THE INVENTION

This invention relates to translation of three-dimensional data to a reference coordinate system, and more particularly to registration of three dimensional image data with an X-ray imaging coordinate system.

BACKGROUND OF THE INVENTION

Interventional medicine is the collection of medical procedures in which access to the site of treatment is made by navigation through one of the subject's blood vessels, body cavities or lumens. Interventional medicine technologies have been applied to manipulation of medical instruments which contact tissues during surgical navigation procedures, making these procedures more precise, repeatable and less dependent of the device manipulation skills of the physician. Some presently available interventional medical systems for directing the distal tip of a medical device from the proximal end of the medical device use computer-assisted navigation and a display means for providing a visual display of the medical device along with anatomical images obtained from a separate imaging apparatus. Such systems can provide a visual display of blood vessels and tissues, obtained from a Fluoroscopy (X-ray) imaging system for example, and can display a projection of the medical device being navigated to a target destination using a computer that controls the orientation of the distal tip of the medical device.

In some cases, it may be difficult for a physician to become oriented in a three dimensional setting using a display of a single-plane X-ray image projection. Enhancement or augmentation of the single-plane X-ray image may be required to aid the physician in visualizing the orientation of the medical device and three-dimensional tissue surfaces and objects in the body. A method is therefore desired for enhancing a display image of the medical device and anatomical surfaces to include three-dimensional images of surfaces and objects in the body.

SUMMARY OF THE INVENTION

The present invention relates to a method for determining a transformation of a three-dimensional pre-operative image data set to obtain a registration of the three-dimensional image data with an X-ray image of a subject body. In one aspect of the present invention, the method comprises the steps of the user identifying at least two extreme opposing points on the object in the subject from at least one X-ray image plane, obtaining from the image data a set of contour points for each of a plurality of section-planes, performing a projection of every contour point in a sampling of the plurality of section-planes, and selecting from the sampling the section-plane with the contour point projecting nearest to the user-identified extreme point. The method further comprises the steps of the user identifying a three-dimensional center point of the object relative to the X-ray imaging coordinate system, defining a first grid having a predetermined number of intervals at a predetermined interval spacing with the grid center at a user-identified center of the pre-operative image, performing a projection of the center of the three-dimensional image data set onto each grid point for evaluation, and selecting the grid point that when projected minimizes a cost function, where the selected grid point is used to define a translation matrix for registering the three-dimensional contour data with a three-dimensional X-ray coordinate system. This method enables registration of a three-dimensional image object such as an organ to an X-ray imaging system, for suitable overlay onto the X-ray image projection.

In another aspect of the present invention, the method may further refine the search for the closest fit section-plane by defining a narrower sampling of a predetermined number of neighboring section planes on each side of the previous section-plane selected from the prior sampling. The method performs a projection of each contour point on a predetermined number of sequential section-planes that neighbor the previously selected section-plane to create a narrower data set of section-planes and contour points for evaluation, and selecting the section-plane with the contour points projecting nearest to the user-identified extreme points based on minimizing a cost function.

In another aspect of the present invention, the method may further refine the search for the closest fit grid point by iteratively defining a succeeding grid having a predetermined number of intervals at an interval spacing substantially smaller than the preceding grid spacing, with the grid center at the point selected in the preceding grid, performing a projection of the center of the three-dimensional image data set onto each point in the successive grid for evaluation, selecting a grid point that when projected minimizes a cost function.

Further aspects of the present invention will become apparent from the detailed description provided hereinafter. It should be understood that the detailed description and specific examples, while indicating various embodiments and methods of the invention, are for illustration purposes only and are not intended to limit the scope of the invention.

BRIEF DESCRIPTION OF THE DRAWINGS

Corresponding reference numerals indicate corresponding points throughout the several views of the drawings.

DETAILED DESCRIPTION OF THE INVENTION

In one embodiment of the present invention, a method is provided for determining a transformation of a three-dimensional pre-operative image data set to obtain a registration of three-dimensional image data with an X-ray imaging system. The method comprises the steps of identifying at least two extreme opposing points on the object in the subject from at least one X-ray image plane, obtaining from the image data a set of contour points for each of a plurality of section-planes, performing a projection of every contour point in a sampling of the plurality of section-planes, and selecting from the sampling the section-plane with the contour point projecting nearest to the user-identified extreme point. The method further comprises the steps of identifying a three-dimensional center point of the object relative to the X-ray imaging coordinate system, defining a first grid having a predetermined number of intervals at a predetermined interval spacing with the grid center at the user-identified center of the pre-operative image, performing a projection of the center of the three-dimensional image data set onto each grid point for evaluation, and selecting the grid point that when projected minimizes a cost function. The selected grid point is used to define a translation matrix for registering the three-dimensional contour data with a three-dimensional X-ray coordinate system. Given the contour of an organ, such as a heart, information on the contour from an X-ray projection may be used to register to a pre-operative three-dimensional image.

Figure 1:
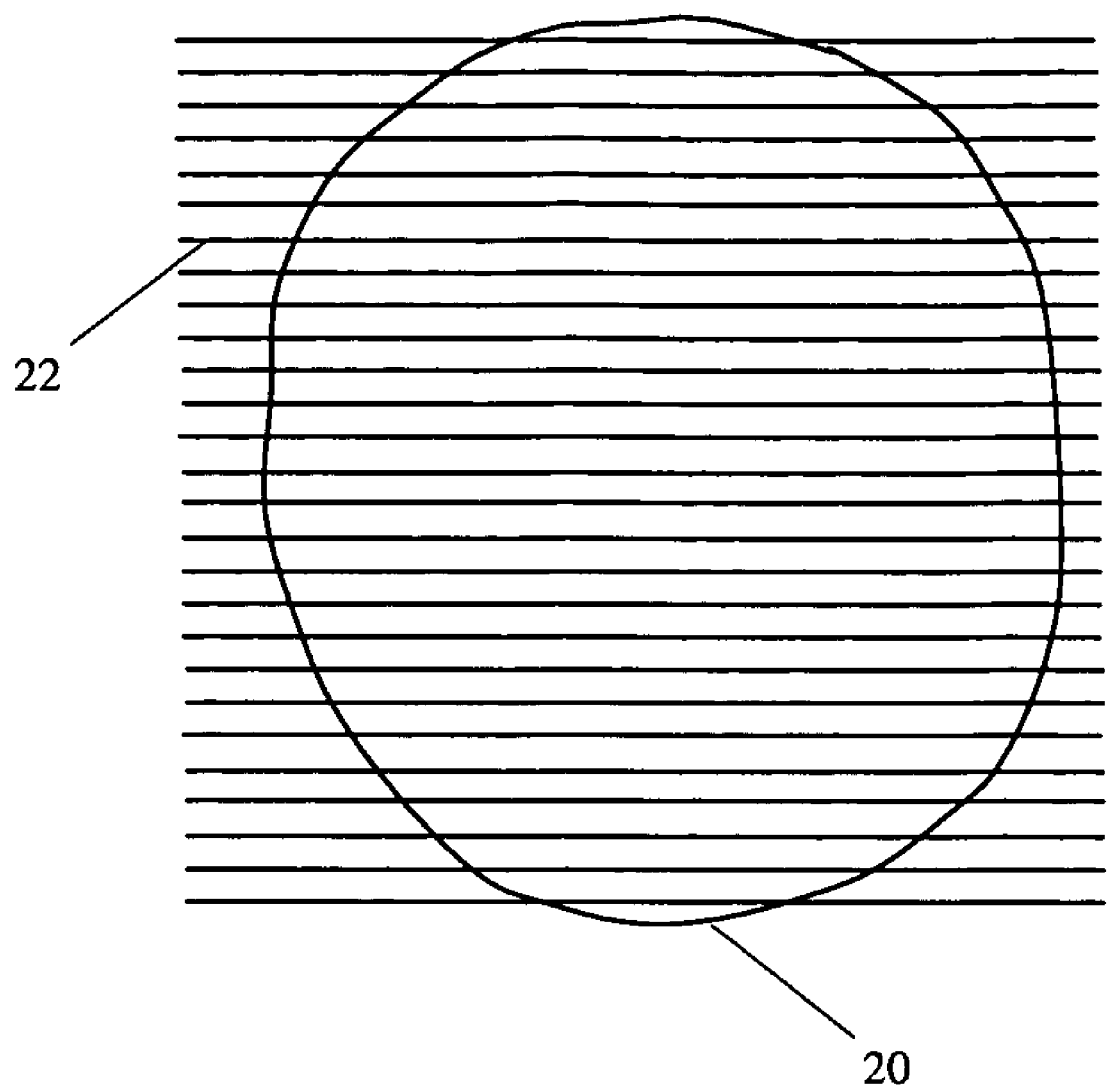
FIG. 1 is an illustration of a pre-operative three-dimensional image object divided into a plurality of section views.
Figure 2:
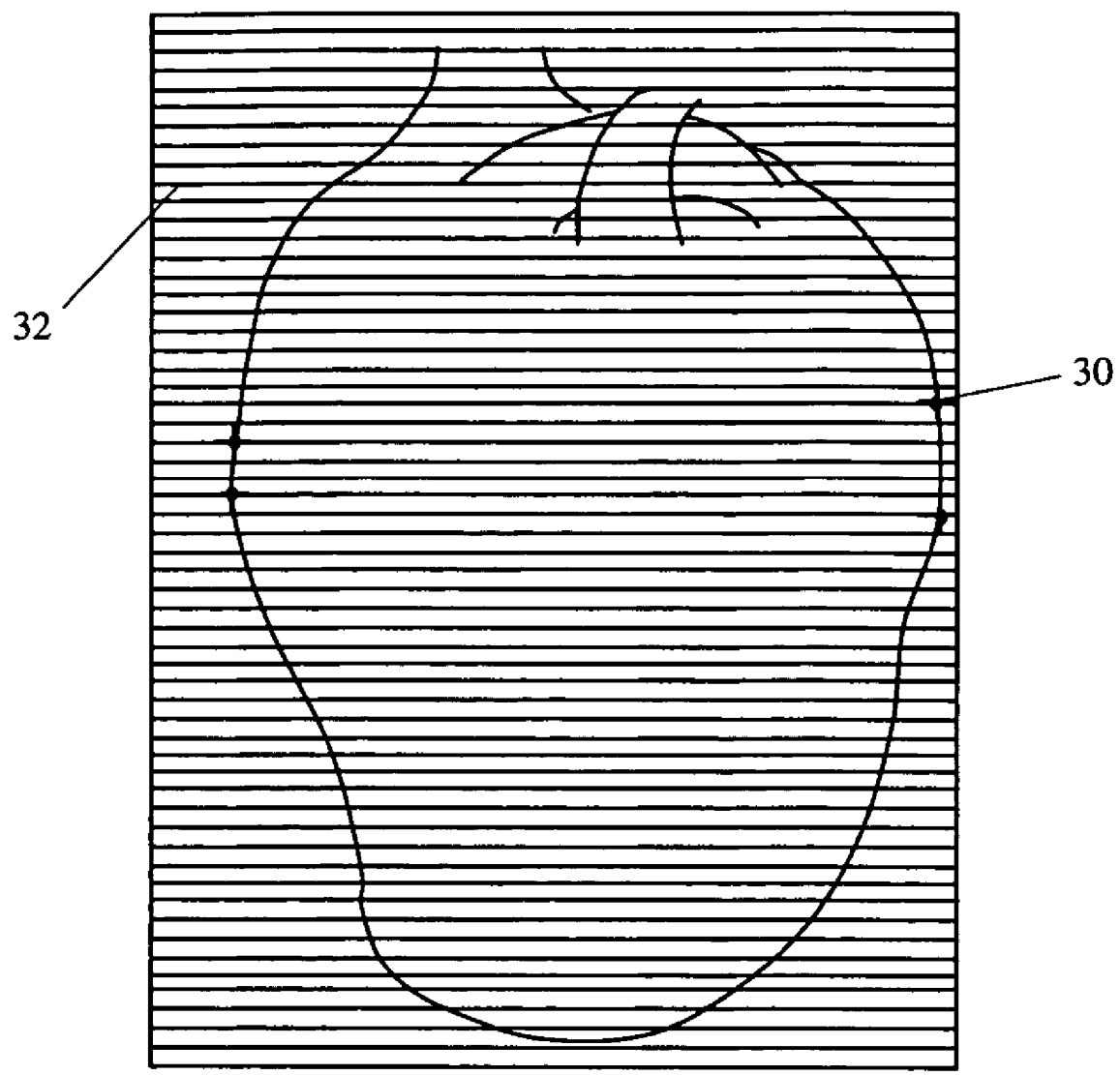
FIG. 2 is an illustration of a section view showing at least two extreme opposite points on the contour of the pre-operative image in accordance with the principles of the present invention.

As shown in FIG. 1, one embodiment of the present invention relates to a method for determining a desired transformation of a three dimensional pre-operative image data set for obtaining a "registration" of a pre-operative image 20, such as an organ, to an X-ray image system. The registration of a three-dimensional image 20 will allow, among other things, overlay of a visual representation of a pre-operative image object onto an X-ray image plane, which can serve as both a visual tool and an aid in surgical navigation. It is assumed for such an image object that the X-ray geometry, or source-to-image distance data, is available, and that the pre-operative image data is oriented correctly with respect to the X-ray imaging plane. The method involves pre-processing the three-dimensional pre-operative image data set to obtain a set of contour points, including points at or near opposing extreme ends of the image object in each of a plurality of sectional planes 22, which establish a three-dimensional contour point data base for a plurality of section-planes 22. In one embodiment of the present invention, the image object volume 20 is divided into about 150 section-planes 22 shown in FIG. 1. Each section-plane 22 is divided by about ninety interval lines 32 which intersect the contour of the image object 20 at the left and right sides as shown in FIG. 2, to define a set of contour points 30 for each section-plane 22. The three-dimensional image object is now defined by a set of 150 planes, each having about 180 data points.

The method further includes the steps of having the user identify an approximate volume center for the object displayed in an X-ray image, in at least two X-ray image planes to establish a three-dimensional center data point. The method also includes the step of identify at least two contour points at the extreme left and extreme right sides of the object from at least one X-ray image plane $(X_{i,L})$. The user interacts with the X-ray system to locate a point corresponding to an approximate center of the object contour on a first X-ray image display plane and a second X-ray image display plane. This selects a three-dimensional point that will be used as the center of a grid about which a search will be performed. The user also locates a total of at least two extreme left lateral and extreme right lateral points $(X_{i,L})$ from at least one X-ray image display. Alternatively, a default volume center could be used, or extreme points on the outline of the image object other than left or right could be used.

Figure 3:
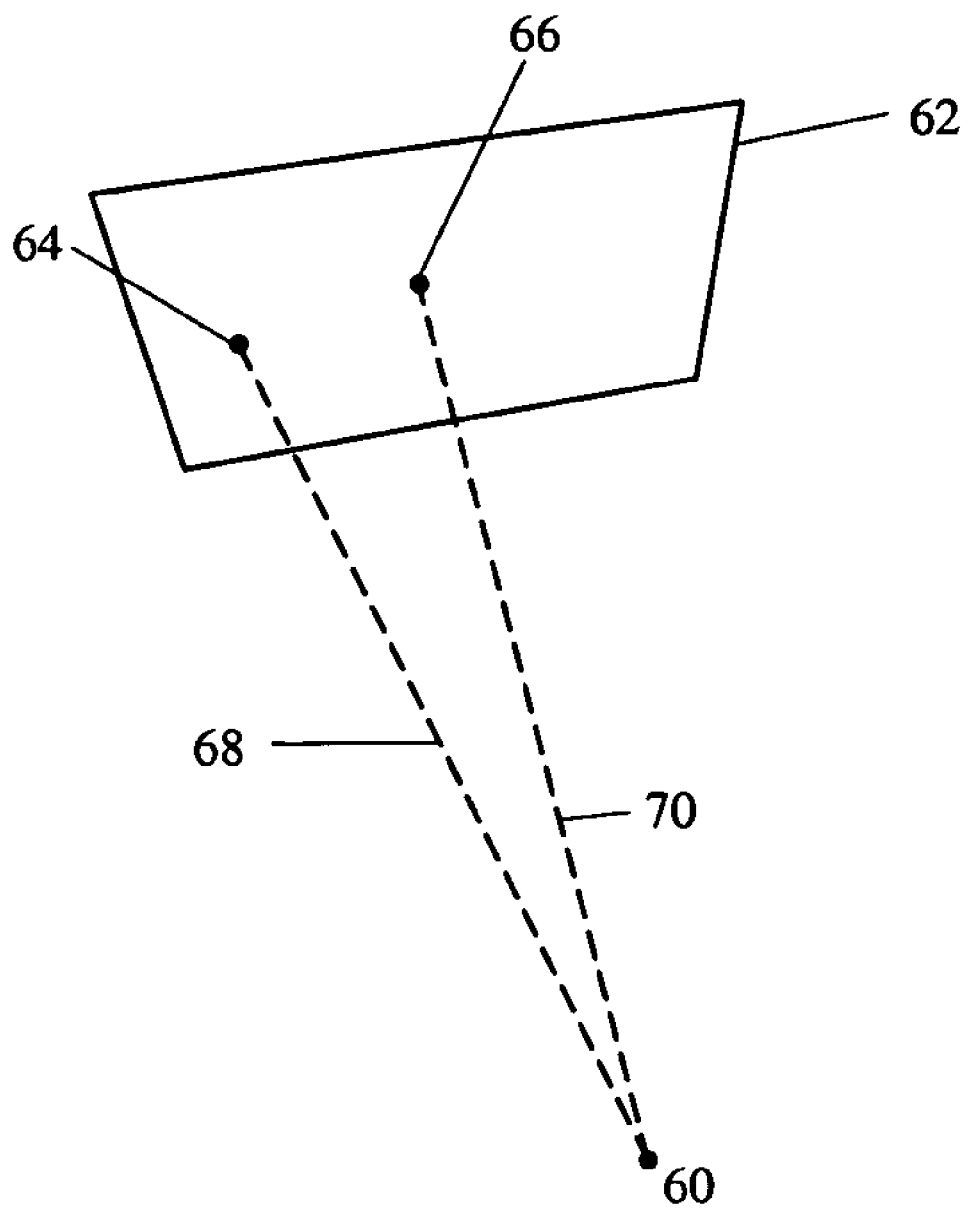
FIG. 3 is an illustration of an X-ray source and image plate, and the projection of points onto the image plate in accordance with the principles of the present invention.

The method further comprises the steps of performing a projection of every contour point 30 on a sampling of all the section-planes 22 onto the X-ray image plane 62, and using a transformation matrix derived from source-to-image distance 68 and source-to-isocenter (66) distance 70 as shown in FIG. 3. In FIG. 3, a geometric illustration is shown of an X-ray source point of origin 60 for emitting a beam towards a subject and the imaging plane 62. The projection of a point 30, or $\vec{x}$, from a section plane 22 onto the imaging plane 62 as a perspective projection point 64, or $\vec{x}_p$, can be obtained using a projection matrix. The projection of these contour points establishes a set of projection points to be evaluated relative to the user-picked extreme data points $(X_{i,l})$ from the X-ray image, for determining from the sampling the select section-plane 22 with points 30 that project nearest to the user-picked extreme data points $(X_{i,l})$, by minimizing a cost function. The cost function determines the distance between the projection points and user-picked extreme points $(X_{i,l})$.

The method may further refine the above search by defining a narrower sampling of a predetermined number of neighboring section planes on each side of the previously selected section-plane from the prior sampling. The method performs a projection of every contour point on a predetermined number of sequential section-planes that neighbor the previously selected section-plane, and selects from this narrower sampling the section-plane with the points projecting nearest to the user-identified extreme points based on minimizing a cost function. This method determines from the refined sampling the best-fit section plane with the data points closest to the user identified points from the X-ray image.

The method provides for projection of the section-plane contour point, x to a projected point $x_p$, defined as:

$$x_P = x_C + \frac{d}{(d - n \cdot (x - x_C))} A(x - x_C) \quad (1)$$

where $x_C$ is the X-ray plate center 66 coordinates, d is source to image distance 68, n is the normal to the X-ray plane pointing towards the isocenter, and A is a 3×3 matrix product. With $b_0$ equal to the source-to-isocenter distance 70, the center of the plate 62 is given by $x_{C,0}=(0, 0, d-b_0)$, where the isocenter is at the origin of a coordinate system having axis z (anterior), y (superior) and x (left lateral). Thus, n=−Rz, and for Left Anterior Oblique and Right Anterior Oblique rotations, R is defined as:

$$R = \begin{pmatrix} \cos\theta & 0 & \sin\theta \\ 0 & 1 & 0 \\ -\sin\theta & 0 & \cos\theta \end{pmatrix} \quad (2)$$

where $\theta > 0$ is a Left Anterior Oblique rotation and $\theta < 0$ is a Right Anterior Oblique rotation. The projected point in local plate coordinates is given by $$\vec{y} = (I - nn^T)\vec{q} \text{ or } R\vec{x} - \vec{n}(\vec{n} \cdot R\vec{x}) \quad (3)$$

The point $x_p$ is local plate coordinates is defined as $x_1 = (x, y, 0)$ and the projected point is:

$$x_P = Rx_l + x_C,$$

where $$x_l = \frac{d}{(d - n \cdot (x - x_C))} R^T A (x_P - x_C)$$

which leads to:

$$x_C = Rx_{C,0} \quad (4)$$

For each section-plane, the contour points are projected using the above equation (4). An index of the corresponding projection points may be called m(j) for each plane j. For the set of planes chosen, it is desired to find a plane j* that minimizes the distance:

$$|x_{m(j)} - x_{i,l}|^2 \quad (5)$$

for the specific projection j and left-right index i. This step of finding the plane that minimizes equation (5) may be repeated and further refined by choosing thirty-one successive section-planes centered around the selected j* plane at which the minimum distance was found in the prior set of planes chosen. The contour points in the refined set of 31 section planes can be evaluated to find the section plane that minimizes equation (5) above.

This is the point, indexed by m(j*(i,l)), that projects nearest to $(X_{i,L})$. The method then calls for projection using equation (4) of each extreme point picked by the user $(X_{i,L})$, and evaluates them using the cost function given below:

$$C = \Sigma_{i,l} |x_{m(j)} - x_{i,l}|^2 \quad (6)$$

In a preferred embodiment, the method then defines a 9×9×9 grid having a spacing of 2 cm and a center at the user-identified three-dimensional center point taken from the two or more X-ray image planes. The method performs a projection of the center of the three-dimensional image data set for each of the grid points and uses the cost function to select the grid point that when projected minimizes a cost function. This is the grid point that projects nearest to the user-identified center point. It should be noted that other embodiments may alternatively comprise different grid sizes that could be more convenient.

In one embodiment of the present invention, the method iteratively defines a succeeding 9×9×9 grid having a spacing of preferably 0.5 cm and a center about the last selected point that projected nearest to the user-identified center. The method performs a projection of the center of the three-dimensional image data set for each of the grid points, and evaluates the grid points that when projected minimizes a cost function to select the succeeding grid point with the minimum cost function as a succeeding point that projects nearest to the user-identified center point. About the selected grid point, another finer grid having a spacing of preferably 0.625 millimeter is successively established and similarly evaluated. This iterative process of reducing the grid interval spacing is repeated until a grid point having a cost function of less than a predetermined value is obtained. A translation T=(Cn−V) may then be written using this obtained point, for use in translating a three-dimensional image data set to the three-dimensional X-ray coordinate system. This enables registration of a three-dimensional image data set with an X-ray image, to enable overlay of a visual representation of the pre-operative image on the X-ray display.

The advantages of the above described embodiment and improvements should be readily apparent to one skilled in the art, as to enabling determining a transformation for use in obtaining registration of a three-dimensional image object with an X-ray image display. Additional design considerations may be incorporated without departing from the spirit and scope of the invention. Accordingly, it is not intended that the invention be limited by the particular embodiment or form described above, but by the appended claims.

What is claimed is:

1. A method for obtaining a registration of three-dimensional image data with an X-ray imaging system, the method comprising the steps of:
   obtaining a set of contour points for an image object in each of a plurality of section-planes;
   a user identifying at least two extreme opposing points on the object in a subject body from at least one X-ray image plane;
   performing a projection of each contour point on a sampling of the plurality of section-planes for evaluation;
   selecting the section-plane with the contour point projecting nearest to the user-identified extreme point;
   the user identifying a three-dimensional center point of the object relative to a X-ray imaging coordinate system;
   defining a first grid having a predetermined number of intervals at a predetermined interval spacing with the grid center at the user-identified center of the pre-operative image, performing a projection of the center of the three-dimensional image data set onto each grid point for evaluation, and selecting the grid point that when projected minimizes a cost function;
   iteratively defining a succeeding grid having a predetermined number of intervals at an interval spacing substantially smaller than the preceding grid spacing, with the grid center at the point selected in the preceding grid, performing a projection of the center of the three-dimensional image data set onto each point in the successive grid for evaluation, selecting a grid point that when projected minimizes a cost function, and repeating the iterative step until a grid point that projects within a predetermined minimum is obtained; and
   defining a translation using the obtained point for registering the three-dimensional contour data with the X-ray imaging coordinate system.

2. The method of claim 1, wherein evaluation of the projected contour points comprises determining a minimum distance function between the projection of the contour points in the section plane and the user-picked extreme points.

3. The method of claim 2, wherein the distance function determines an absolute value of the distance between points.

4. The method of claim 1, wherein the sampling of section planes are evenly spaced.

5. The method of claim 1, wherein the sampling of section planes is less than a quarter of the total number of section planes.

6. The method of claim 1, wherein the user identifies a center point of the object in at least two X-ray image planes to establish a three-dimensional center point.

7. The method of claim 6, wherein the evaluation of the projection points comprises a cost function.

8. The method of claim 7, wherein the evaluation of the projection points comprises a cost function based on the sum of the absolute distances between the projection points from the section-plane and the user-picked extreme points.

9. A method of obtaining a registration of three-dimensional image data to an X-ray imaging system, the method comprising the steps of:
   a user identifying a center point of an object in a subject in at least two X-ray image planes to establish a three-dimensional center point
   the user identifying at least two extreme opposing points on the object in the subject from at least one X-ray image plane;
   obtaining from the image data a set of contour points for each of a plurality of section-planes,
   performing an iterative step of defining a sampling of the plurality of section planes and performing a projection of every contour point in the sampling of section-planes, selecting from the sampling the section-plane with projection points having a least distance function relative to the user-identified extreme points, and repeating the iterative step until a section-plane is obtained in which the least distance function between the projected points and the user-identified extreme points is less than a predetermined amount;

performing the iterative step of defining a grid having a predetermined number of intervals at a predetermined spacing where the spacing is successively smaller than a preceding grid, performing a projection of the center of the three-dimensional image data set onto each grid point for evaluation, and selecting the grid point at which the projection yields a minimized cost function, and repeating the iterative step until a grid point is obtained that yields a cost function value less than a predetermined amount; and defining a translation matrix based on the selected grid point that can be used to obtain registration of the three-dimensional image data with an X-ray imaging coordinate system.

10. The method of claim 9, wherein the least distance function of the projected contour points comprises determining an absolute minimum distance between the projection of the contour points in the section plane and the user-picked extreme points.

11. The method of claim 10, wherein the evaluation of the projection points comprises a cost function based on a sum of absolute distances between the projection points and the user-picked extreme points.

12. The method of claim 11, wherein the iterative step of defining a sampling of section-planes comprises selecting a first sampling of a predetermined number of evenly spaced section-planes from the plurality of section-planes.

13. The method of claim 12, wherein the iterative step of defining a sampling of section-planes further comprises defining a second refined sampling of a predetermined number of sequential section-planes on each side of the section-plane selected from the first sampling.

14. The method of claim 11, wherein the iterative step of defining a grid comprises defining a first grid that is centered on the user-identified center point of the object in the subject.

15. The method of claim 14, wherein the iterative step of defining a grid comprises defining a second grid having a spacing smaller than that of the first grid, the second grid being centered on the grid point selected from the first grid that yielded a minimized cost function.

16. The method of claim 15, wherein the iterative step of defining a grid comprises defining a third grid having a spacing smaller than that of the second grid, the third grid being centered on the grid point selected from the second grid that yielded a minimized cost function.

17. The method of claim 16, wherein the user identifies a center point of the object in at least two X-ray image planes to establish a three-dimensional center point.

18. The method of claim 16, wherein the transformation matrix is defined by a grid point selected from the third grid that yields a cost function value that is less than a predetermined value.

19. A method of obtaining a registration of three-dimensional image data to an X-ray imaging system, the method comprising the steps of:

a user identifying a center point of an object in a subject in at least two X-ray image planes to establish a three-dimensional center point the user identifying at least two extreme opposing points on the object in the subject from at least one X-ray image plane;

obtaining from the image data a set of contour points for each of a plurality of section-planes, selecting a first sampling of a predetermined number of evenly spaced section-planes from the plurality of section-planes, performing a projection of every contour point in the sampling of section-planes, selecting from the first sampling the section-plane with projection points having a least distance function relative to the user-identified extreme points;

selecting a second refined sampling of a predetermined number of sequential section-planes on each side of the section-plane selected from the first sampling, performing a projection of every contour point in the second sampling of section-planes, selecting from the second sampling the section-plane with projection points having a least distance function relative to the user-identified extreme points;

defining a first grid centered on the user-identified center point of the object in the subject and having a predetermined number of intervals at a predetermined spacing, performing a projection of the center of the three-dimensional image data set onto each grid point for evaluation, and selecting a first grid point at which the projection yields a minimized cost function;

defining a second grid centered on the selected first grid point and having a spacing smaller than that of the first grid, performing a projection of the center of the three-dimensional image data set onto each grid point for evaluation, and selecting a second grid point at which the projection yields a minimized cost function;

defining a third grid centered on the selected second grid point and having a spacing smaller than that of the second grid, performing a projection of the center of the three-dimensional image data set onto each grid point for evaluation, and selecting a third grid point at which the projection yields a minimized cost function; and defining a translation matrix based on the selected third grid point that can be used to obtain registration of the three-dimensional image data with an X-ray imaging coordinate system.

20. The method of claim 19, wherein the evaluation of the projection points comprises a cost function based on a sum of absolute distances between the projection points and the user-picked extreme points.

* * * * *

UNITED STATES PATENT AND TRADEMARK OFFICE
CERTIFICATE OF CORRECTION

PATENT NO.       : 7,657,075 B2                                    Page 1 of 1
APPLICATION NO. : 11/429665
DATED            : February 2, 2010
INVENTOR(S)      : Raju R. Viswanathan It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 943 days.

Signed and Sealed this

Thirtieth Day of November, 2010

David J. Kappos
*Director of the United States Patent and Trademark Office*